United States Patent
Kneer

(10) Patent No.: US 6,478,768 B1
(45) Date of Patent: Nov. 12, 2002

(54) IMPLANT SYRINGE

(75) Inventor: Roland Kneer, Farchant (DE)

(73) Assignee: Gaplast GmbH, Altenau (DE)

( * ) Notice: Subject to any disclaimer, the term of this patent is extended or adjusted under 35 U.S.C. 154(b) by 0 days.

(21) Appl. No.: 09/485,258

(22) PCT Filed: Jul. 22, 1998

(86) PCT No.: PCT/DE98/02057

§ 371 (c)(1),
(2), (4) Date: Feb. 7, 2000

(87) PCT Pub. No.: WO99/07434

PCT Pub. Date: Feb. 18, 1999

(30) Foreign Application Priority Data

Aug. 8, 1997 (DE) .......................... 197 34 385

(51) Int. Cl.[7] .......................... A61M 31/00; A61M 5/315
(52) U.S. Cl. .......................... 604/60; 604/218
(58) Field of Search .............................. 604/59, 60–64, 604/110, 218, 227, 181, 187; 600/564, 431, 432, 7; 606/167

(56) References Cited

U.S. PATENT DOCUMENTS 4,597,753 A * 7/1986 Turley .......................... 227/67
4,820,267 A * 4/1989 Harman .......................... 604/60
5,695,463 A * 12/1997 Cherif-Cheikh ............. 604/171

FOREIGN PATENT DOCUMENTS

| EP | 0 531 036 | * | 3/1993 |
| EP | 0 858 813 A2 | * | 8/1998 |
| WO | WO 84/00304 | * | 2/1984 |

* cited by examiner

Primary Examiner—Michael J. Hayes
(74) Attorney, Agent, or Firm—Pyle & Piontek

(57) ABSTRACT

The implant syringe has a spacer which limits the advance movement of the plunger into the syringe needle in such a way that a distance equivalent to the length of the strand-shaped preparation to be discharged remains between the outlet orifice of the syringe needle and the head end of the plunger. The syringe needle is connected to a grip member that can be retracted over a distance coinciding with the length of the preparation. An insertion channel is initially made with the implant syringe in the body of a patient. Subsequently, the preparation to be discharged is pushed forward to the tip of the needle by advancing the plunger, whereupon the syringe needle is retracted to such an extent that the head end of the plunger reaches or projects beyond the tip of the needle.

9 Claims, 2 Drawing Sheets

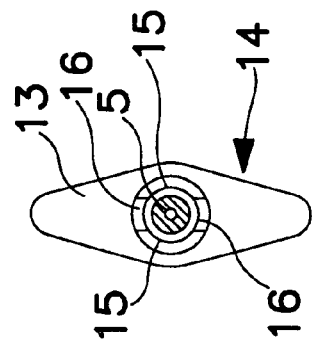
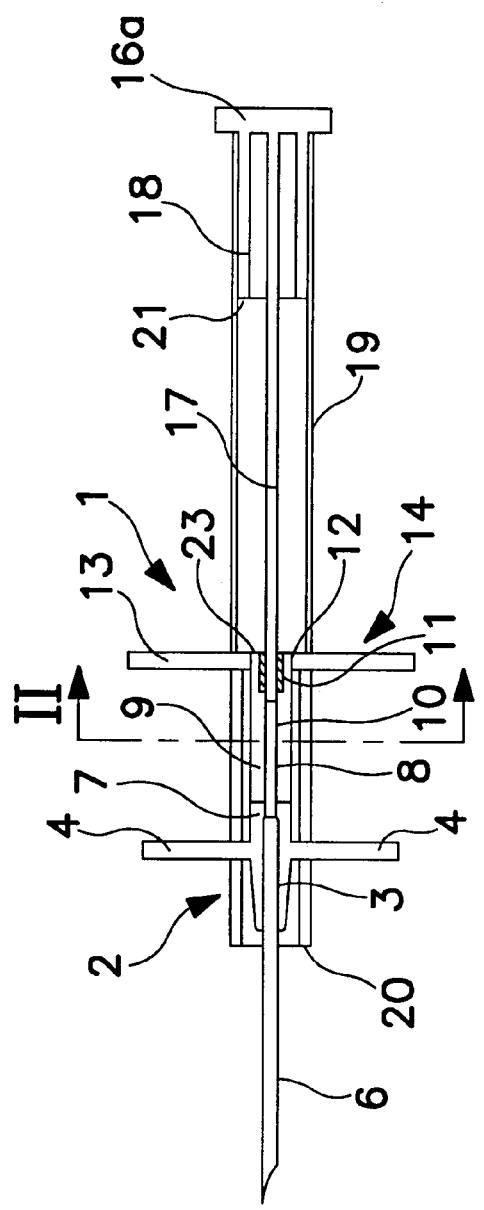

IMPLANT SYRINGE

The present invention relates to an implant syringe from the needle of which a preferably elongated strand-shaped preparation with a sustained release substance is discharged by means of a plunger. Most of the time such a sustained release preparation is placed in a patient's abdominal wall which has previously been pierced with the needle of the implant syringe to form a receiving channel for the preparation.

So far one has proceeded such that after formation of the insertion channel the plunger of the implant syringe is pushed forward into the syringe needle while the entire implant syringe with the syringe needle is simultaneously retracted from the insertion channel, whereby the preparation slowly exits out of the syringe needle and finally leaves said needle. The problem arises here that the advance movement of the plunger and the retraction of the syringe needle have to be timed such that the preparation, which is a solid shaped body, is exactly placed in the insertion channel. In cases where the preparation is pressed out of the syringe needle at a pace faster than that at which the needle is retracted in the insertion channel, the preparation is violently pushed into the tissue of the abdominal wall, thereby causing great pain for the patient. On the other hand, if the syringe needle is retracted at a pace faster than that at which the preparation exists from the needle, this may have the consequence that the strand-shaped tablet is not completely received in the insertion channel.

It is the object of the present invention to provide an implant syringe by which it is ensured that the preparation is exactly placed in the insertion channel so that the placement is carried out without any pain, except for the one caused by the formation of the insertion channel.

According to the invention said object is achieved by the features of patent claim 1.

Advantageous developments of the invention are characterized in the subclaims.

The implant syringe according to the invention comprises a spacer which limits the advance movement of the plunger into the syringe needle in such a way that a distance equal to the length of the preparation to be discharged or slightly greater than said length remains between the outlet orifice of the syringe needle and the head end of the plunger in the forwardly pushed preparation-discharging position. Moreover, the syringe needle can be retracted by means of a grip member towards the spacer by a distance which is at least as great as or also greater than the length of the preparation.

Thus, in the implant syringe according to the invention, the plunger is pushed forward in a first step up to the abutment formed by the spacer after placement of the syringe and formation of the insertion channel, whereby the strand-shaped tablet contained in the implant syringe is pushed foward up to the tip of the needle, whereupon, while the plunger is immovably held, the syringe needle is retracted by means of an appliance or handle at least to such an extent that the preparation is exposed. It is thereby ensured in a reliable manner that the strand-shaped preparation is not pushed forward beyond the needle tip, i.e. beyond the end of the insertion channel, i.e. it is impossible to press the solid tablet strand into the tissue of a patient.

Since the preparation is moved by the advance movement of the plunger into a position in which it is located at the needle tip and thus at the end of the insertion channel, it is also ensured that it is placed over its entire length in the insertion channel as the preparation is not retracted while exiting from the syringe needle. Instead, the syringe needle is withdrawn from the preparation while the latter is held in its position by the plunger. While the syringe needle is retracted, the front surface of the syringe housing surrounding the rear portion of the syringe needle should remain in contact with the patient's skin when said front surface of the housing serves to limit the length or depth of the insertion channel, as is preferred.

In a preferred development of the present invention, the implant syringe according to the invention consists essentially of three main components, namely the spacer, the base plate preferably extending at a right angle relative to the longitudinal axis of the syringe, and a guide sleeve which is attached thereto and forms the above-mentioned syringe housing and whose front surface should limit the insertion depth of the syringe needle; furthermore, it consists of the grip member which as a handle preferably contains two tabs that are positioned in a plane parallel to the base plate of the spacer and project from an essentially tubular needle holder of the grip member that extends in the axial direction of the syringe, with the needle holder containing an axial through hole in which the syringe needle is seated, e.g. pressed thereinto, and of the plunger which has the shape of an elongated thin rod and which is centrally seated on an end plate that has molded thereon a sleeve which surrounds the end section of the plunger and limits the advance movement of the plunger as soon as its front face impinges on the base plate of the spacer.

In detail, it is advantageously suggested that the essentially tubular central attachment of the grip member, which forms the needle holder, should have an axial through hole engaged by the syringe needle. The syringe needle, however, extends preferably not entirely through the hole of the needle holder but leaves a rear end section of the through hole unoccupied which in this instance has a restricted free inner diameter slightly smaller than the inner diameter of the syringe needle and above all slightly smaller than the outer diameter of the strand-shaped preparation. The inner diameter of the end section of the through hole can be reduced by the measure that individual projections, which e.g. may be shaped in the form of beads or noses, slightly project inwards, the projections being dimensioned such that a strand-shaped tablet engaging into said end section of the through hole is prevented from entering into the syringe needle without the action of the plunger, and thus from unintentionally sliding out of the implant syringe. The preparation, however, is not so firmly retained in the end section of the through hole that the advance movement into the syringe needle as effected by the plunger would be impeded.

The grip member as a handle for retracting the syringe needle preferably comprises two opposite tabs projecting from the tubular needle holder, without the invention being limited to such a configuration.

The rear end of the essentially tubular needle holder is suitably connected to an element which is also essentially tubular and serves to receive the strand-shaped preparation, the preparation receiving element having a through hole which is in alignment with that of the needle holder. The two plastic elements may e.g. be put together or connected to each other in any other suitable manner by means of their front faces. Suitably, they have the same cross-sectional shape with a coinciding outer diameter, and the diameter of the through hole should here be slightly greater than the outer diameter of the preparation.

Suitably, the strand-shaped preparation is inserted into the through hole of the preparation receiving element before the grip member composed in the above-described manner is assembled with the spacer and the guide sleeve thereof.

The spacer suitably includes a base plate having a central hole in which in the initial state of the implant syringe the rear end of the preparation receiving element is seated, and a guide sleeve which extends in axial direction and projects from the base plate at a right angle. The guide sleeve preferably comprises two opposite and axially uninterrupted slots, i.e. it consists of two spaced-apart guide sleeve sections, with the tabs of the grip member passing through said slots and projecting outwards beyond the guide sleeve, so that they can be gripped from behind by the fingers of a user of the implant syringe to retract the syringe needle for discharging the preparation. This will be described in more detail further below.

The rear end section of the preparation receiving element has suitably seated therein a sealing ring for the plunger which in the initial state of the syringe engages with its front head end over a small distance into the section of the through hole left unoccupied by the preparation. The preparation receiving element is displaceably seated in the central bore of the base plate of the spacer. After the preparation has been discharged, the preparation receiving element can pass over its full length through the base plate of the spacer, which will be explained in more detail further below.

The plunger of the implant syringe is suitably secured to an end plate which has molded thereon the already mentioned sleeve which surrounds a rear plunger section. Said sleeve has an inner diameter greater than the outer diameter of the preparation receiving element and, optionally, of the needle holder. When the syringe needle is retracted, the preparation receiving element will pass through the base plate of the spacer into the interior of the sleeve.

In the initial state of the implant syringe, the sleeve surrounding the rear end section of the plunger is suitably surrounded by a removable spacer element which rests with one end on the base plate of the spacer and with the other end on the end plate of the plunger. Said removable spacer element which may e.g. be a sleeve cut open over its entire length prevents an unintended advance movement of the plunger prior to the use of the implant syringe.

The inventive implant syringe is handled in the following way: first the insertion channel is formed in that the abdominal wall of a patient is pierced by the syringe needle to such a depth that the front edge of the two-part guide sleeve of the spacer rests on the patient's skin. Subsequently, the spacer element is removed. Thereupon, the plunger is advanced by exerting pressure on the end plate which is connected to said plunger, with the base plate of the spacer being gripped from behind. Said operation is completed when the front edge of the sleeve surrounding the plunger impinges on the base plate of the spacer. The strand-shaped preparation is thereby moved forward towards the outlet orifice of the syringe needle.

Subsequently, the grip member is retracted up to an abutment in that its projecting tabs are gripped from behind. The abutment may be created by the rear edge of the preparation receiving element impinging on the end plate of the plunger. The invention is not limited to such a configuration, but it is for instance also possible that the tabs of the grip member impinge on an abutment of the guide sleeve or on the base plate of the spacer. As soon as the abutment has been reached, the preparation is deposited so that the section of the syringe needle still projecting over the guide sleeve can be withdrawn from the insertion channel.

The implant syringe according to the invention is preferably a disposable syringe intended for single use without the invention being limited to such a configuration. The individual components are preferably made from plastics, except for the syringe needle which suitably consists of metal. The needle holder can e.g. be made from polypropylene or polyethylene, such a material being suited for forming the holding noses for the preparation. The adjoining preparation receiving element suitably consists of transparent polycarbonate. The sealing ring of the spacer, for which e.g. polypropylene or polyethylene are suitable materials, suitably consists of an elastomer material. Of course, the invention is not restricted to such materials.

The sustained release preparation to be deposited need not necessarily have a continuous strand-like shape, although this will most of the time be the case. The implant syringe is also usable for depositing a plurality of successively arranged tablets having e.g. a spherical shape.

Further details of the present invention will become apparent from the following description of a preferred embodiment of the invention, in which:

FIG. 1 shows an implant syringe in the initial state;

FIG. 2 is a section through the implant syringe according to FIG. 1 along line II—II in FIG. 1;

Figure 4:
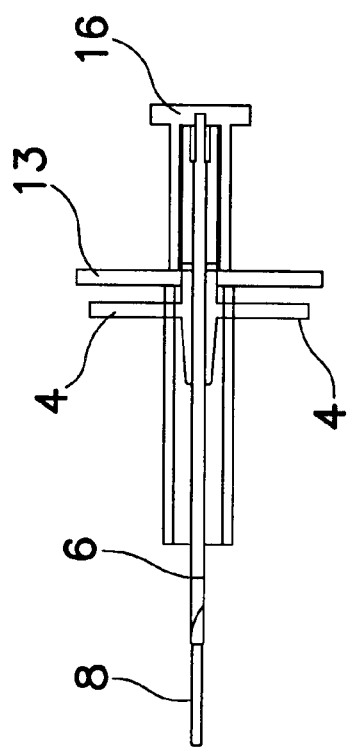
FIG. 4 shows the implant syringe in the retracted state of the needle.

The implant or depot syringe 1 as shown in the figures comprises a grip member designated by 2 on the whole, which consists of a central tubular or sleeve-like needle holder 3 and tabs 4 projecting in a vertical direction therefrom. The needle holder 3 is configured on its section oriented forward away from the tabs in such a manner that it has a slightly conically converging shape.

The through hole 5 of the needle holder 3 has seated therein a syringe needle 6 which preferably consists of metal and does not extend through the whole hole 5 but leaves an end section 7 of the through hole 5 unoccupied. In the area of the end section 7, the free interior space of the through hole 5 is reduced by inwardly projecting noses or beads to such an extent that a strand-shaped preparation 8 is held at said place within a slightly clamping seat which prevents the preparation 8 from independently leaving the implant syringe through the syringe needle 6.

The needle holder 3 is connected to a preparation receiving element 9, for instance, by a plug-type connection which has the same outer diameter as the adjoining section of the needle holder 3. The through hole 10 of the preparation receiving element 9 is in alignment with the through hole 5 of the needle holder 3.

A sealing ring 11 of elastomer is seated in the rear end section of the preparation receiving element 9.

In the state shown in FIG. 1, the end section of the preparation receiving element 9 is seated in a central through hole 12 of the base plate 13 of a spacer which is designated by 14 on the whole. Furthermore, the spacer 14 contains an integrally molded guide sleeve which consists of two guide sleeve sections 15 leaving thereinbetween two diametrically opposed spaces or slots 16. The tabs 4 of the grip member 2 pass through said two slots 16. The grip member 2 is thus movable in axial direction towards the base plate 13 of the spacer 14, the tabs 4 being guided in the slots 16 of the guide sleeve 15, 15.

In the state illustrated in FIG. 1, the head end of an elongated rod-like plunger 17 is seated in the sealing ring 11. The plunger 17 is in alignment with the preparation 8 which, in turn, is in alignment with the syringe needle 6.

The plunger 17 is secured to an end plate 16a which is made integral with a sleeve 18 that surrounds the rear end portion of the plunger 17 at such a distance that the preparation receiving element 9 can enter into the space between the sleeve 18 and the plunger 17, as shown in FIG. 4.

The sleeve 18 is surrounded by a spacer sleeve 19 which is slotted over its entire length and which rests on the base plate 14 and the end plate 16a and prevents the plunger 17 from being pushed forwards. The spacer sleeve 19 is removed before the plunger 17 is pushed forwards.

Figure 3:
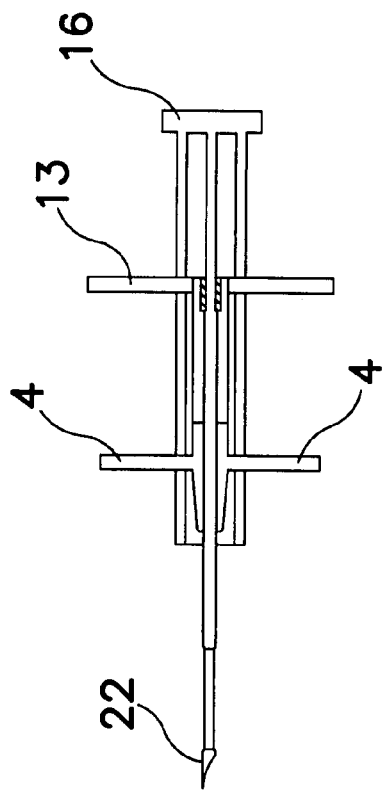
FIG. 3 shows the implant syringe according to FIG. 1 in a state in which the preparation has been pushed forward towards the tip of the needle.

In the state illustrated in FIG. 1, the implant syringe 1 is e.g. stuck into the abdominal wall of a patient until the front edge 20 of the guide sleeve 15 comes to rest on the patient's skin. As shown in FIG. 3, after the spacer sleeve 19 has been removed, the plunger 17 is moved forward by means of the end plate 16 to such an extent to the left side in the figure that the front edge 21 of the sleeve 18 comes to rest on the base plate 14. As a result, the plunger 17 pushes the preparation 8 into the syringe needle 6 and, once within said needle, up to the tip 22 of the needle.

Subsequently, the grip member 2 with the syringe needle 6 is slowly moved back towards the base plate 13 of the spacer 14 by gripping the tabs 4 until the rear edge 23 of the preparation receiving element 9 comes to rest on the end plate 16. The rearward movement of the grip member 2 is conceived such that the head end of the plunger 17 reaches or projects beyond the tip of the needle so that the preparation 8 is released entirely. The syringe can now be removed from the patient, with the preparation 8 remaining in the insertion channel.

The implant syringe 1 is suitably mounted such that after the grip member 2 and the preparation receiving element 9 have been put together the preparation 8 is inserted into the through hole 10. Subsequently, said assembly is combined with the spacer 14, whereupon the plunger 17 is inserted into the end portion of the hole 10 and the spacer sleeve 19 is mounted.

What is claimed is:

1. Implant syringe for injecting a preparation (8), said syringe comprising a needle (16) having an outlet orifice, a needle holder (3), a plunger (17) in said syringe, said plunger movable toward said outlet orifice, a head (17) on said plunger for discharging the preparation from the syringe, a spacer (14) on said syringe mounted in such a manner which is at least equivalent in length to the length of the preparation to be discharged between the outlet orifice of the needle and the plunger head, a grip member (2) movable toward the spacer for retracting the needle at least over a distance coinciding with the length of the spacer, said needle having an axis of movement, a central opening (5) in the needle holder, said syringe needle being firmly seated in said opening, said preparation and said opening having diameters which are substantially equal.

2. Implant syringe according to claim 1, characterized in that the grip member (2) comprises two opposite tabs (4) projecting from the needle holder (3).

3. Implant syringe according to claim 1, characterized in that the spacer (14) comprises a base plate (13) provided with a central hole (12) and a guide sleeve (15) extending in axial direction.

4. Implant syringe according to claim 3, characterized in that the guide sleeve comprises two opposite, axially uninterrupted slots (16) that are penetrated by a tabs (4) of the grip member (2).

5. Implant syringe according to claim 1, characterized in that the rear end of the needle holder (3) is connected to an essentially tubular preparation receiving element (9) whose through hole (10) is in alignment with that of the needle holder (3).

6. Implant syringe according to claim 5, characterized in that a sealing ring (11) for the plunger (1 7) is seated in the rear end section of the preparation receiving element (8).

7. Implant syringe according to claim 5 or 6, characterized in that the preparation receiving element (8) is displaceably seated in the hole (12) of the base plate (13).

8. Implant syringe according to claim 1, characterized in that the plunger is fastened to an end plate (16a) which has molded thereon a sleeve (18) which surrounds a rear plunger section and the inner diameter of which is larger than the outer diameter of a preparation receiving element (9).

9. Implant syringe according to claim 8, characterized in that the sleeve (18) is surrounded by a removable spacer sleeve (19) which in the retracted initial position of the plunger (17) rests on a base plate (13) and on the end plate (16a).

* * * * *